(12) United States Patent
Williams

(10) Patent No.: US 11,998,403 B2
(45) Date of Patent: Jun. 4, 2024

(54) ENDOSCOPE CLEANING DEVICE

(71) Applicant: Covidien LP, Mansfield, MA (US)

(72) Inventor: Justin Williams, Southbury, CT (US)

(73) Assignee: Covidien LP, Mansfield, MA (US)

(*) Notice: Subject to any disclaimer, the term of this patent is extended or adjusted under 35 U.S.C. 154(b) by 160 days.

(21) Appl. No.: 17/363,194

(22) Filed: Jun. 30, 2021

(65) Prior Publication Data
US 2022/0047354 A1 Feb. 17, 2022

Related U.S. Application Data

(60) Provisional application No. 63/066,379, filed on Aug. 17, 2020.

(51) Int. Cl.
*A61B 90/70* (2016.01)
*A61B 1/00* (2006.01)
*A61B 1/018* (2006.01)

(52) U.S. Cl.
CPC .......... *A61B 90/70* (2016.02); *A61B 1/00096* (2013.01); *A61B 1/00101* (2013.01); *A61B 1/018* (2013.01); *A61B 2090/701* (2016.02)

(58) Field of Classification Search
CPC . A61B 90/70; A61B 1/00096; A61B 1/00101; A61B 1/018; A61B 2090/701; A61B 1/00135; A61B 1/00137; A61B 1/126; G02B 23/2476; G02B 27/0006
See application file for complete search history.

(56) References Cited

U.S. PATENT DOCUMENTS

| | | | |
|---|---|---|---|
| 5,386,817 A * | 2/1995 | Jones | A61B 1/00135 600/125 |
| 5,964,004 A * | 10/1999 | Bean | B08B 9/0436 15/104.16 |
| 6,755,782 B2 | 6/2004 | Ogawa | |
| 8,690,764 B2 | 4/2014 | Clark et al. | |
| 10,335,021 B2 | 7/2019 | O'Prey et al. | |
| 2002/0065450 A1 * | 5/2002 | Ogawa | A61B 1/126 600/157 |
| 2012/0108904 A1 | 5/2012 | Ma et al. | |
| 2014/0094650 A1 * | 4/2014 | Schaning | A61B 1/313 606/1 |
| 2014/0261545 A1 * | 9/2014 | Jenkins | A61B 1/00183 134/8 |
| 2014/0277043 A1 * | 9/2014 | Jenkins | A61B 34/30 134/6 |
| 2018/0214016 A1 | 8/2018 | Thommen et al. | |
| 2020/0060536 A1 * | 2/2020 | Rylander | A61B 1/00135 |

FOREIGN PATENT DOCUMENTS

WO 2017006684 A1 1/2017

OTHER PUBLICATIONS

Extended European Search Report issued in corresponding European Application No. 21190880.1 dated Nov. 16, 2021, 8 pages.

* cited by examiner

*Primary Examiner* — Michael J Carey
*Assistant Examiner* — Christen A. Sharpless
(74) *Attorney, Agent, or Firm* — Carter, DeLuca & Farrell LLP

(57) ABSTRACT

A cleaning device enables cleaning of a lens of an endoscope during a surgical procedure to maintain a clear image without having to remove the endoscope from the patient's body. The cleaning device is mountable to an endoscope such that a wiper of the cleaning device is selectively displaced across the lens of the endoscope to remove debris from the lens.

20 Claims, 5 Drawing Sheets

ENDOSCOPE CLEANING DEVICE

CROSS-REFERENCE TO RELATED APPLICATIONS

This application claims the benefit of and priority to U.S. Provisional Patent Application No. 63/066,379, filed Aug. 17, 2020, the entire contents of which is incorporated by reference herein.

TECHNICAL FIELD

The disclosure relates to a minimally invasive surgical instrument and, more particularly, to an endoscope cleaning device for removing debris from a lens of an endoscope.

BACKGROUND

Minimally invasive surgery eliminates the need to make a large incision in a patient, thereby reducing discomfort, recovery time, and many of the deleterious side effects associated with traditional open surgery. Minimally invasive viewing instruments such as, e.g., laparoscopes and endoscopes, provide viewing of internal tissues and/or organs during the minimally invasive surgery.

Laparoscopic surgery involves the placement of a laparoscope in a small incision in the abdominal wall of a patient, to view the surgical site. Endoscopic surgery involves the placement of an endoscope in a naturally occurring orifice, e.g., mouth, nose, anus, urethra, or vagina, to view the surgical site. Other minimally invasive surgical procedures include video assisted thoracic surgery and cardiovascular surgery conducted through small incisions between the ribs. These procedures also utilize scopes to view the surgical site.

A typical minimally invasive viewing instrument, e.g., a laparoscope or an endoscope, includes a housing, an elongated lens shaft extending from one end of the housing, and a lens that is provided in a distal end of the elongated lens shaft. A camera viewfinder extends from the other end of the housing. A camera is connected to the housing and transmits images sighted through the lens to an external monitor on which the images are displayed. During a surgical procedure, the distal end portion of the elongated lens shaft is extended into the patient, while the proximal end portion of the elongated lens shaft, the housing and the camera viewfinder remain outside the patient. In this manner, the laparoscope/endoscope is positioned and adjusted to view particular anatomical structures in the surgical field on the monitor.

During insertion of an endoscope or a laparoscope into the body and during the surgical procedure, debris, e.g., organic matter and/or moisture, may be deposited on the lens of the scope. The buildup of debris and condensation on the lens impairs visualization of the surgical site, and often necessitates cleaning of the lens.

SUMMARY

The disclosure describes an endoscope cleaning device that demonstrates a practical approach to meeting the performance requirements and overcoming usability challenges associated with cleaning a lens of an endoscope during a surgical procedure.

In accordance with this disclosure, a surgical kit includes an endoscope having a lens at a distal end portion of the endoscope, and a cleaning device including a sleeve and a frame. The sleeve defines a lumen dimensioned to receive the distal end portion of the endoscope. The frame includes a supporting portion, a wiper, and an engaging portion. The supporting portion is secured to the sleeve. The engaging portion is pivotably coupled to the supporting portion and extends distally from the supporting portion. The engaging portion supports the wiper for movement as a single construct. The engaging portion is transitionable between an aligned position, in which, the wiper of the frame is placed in a first position on the lens, and an offset position, in which, the engaging portion is pivoted relative to the supporting portion, whereby the wiper is displaced across the lens to a second position diametrically opposing the first position to remove debris from the lens.

In an aspect, the cleaning device may be integrally formed as a single construct.

In another aspect, the supporting portion and the engaging portion may be monolithically formed.

In yet another aspect, the sleeve may be formed of a flexible or resilient material.

In still yet another aspect, the sleeve may be formed of an elastomer to detachably secure the sleeve to the endoscope.

In an aspect, the cleaning device may further include a lip extending radially inwards from the sleeve and defining an opening in registration with the lens of the endoscope.

In another aspect, the cleaning device may further include a rib extending along a length of the sleeve and over the lip to limit proximal displacement of the sleeve when the lip engages the endoscope.

In still another aspect, the supporting portion of the frame may include opposing lateral portions interconnected by a connecting portion.

In still yet another aspect, the supporting portion may include an arcuate profile corresponding to contour of the sleeve.

In still yet another aspect, the supporting portion may be over-molded to the sleeve.

In still yet another aspect, the wiper may include a tapered edge.

In still yet another aspect, the engaging portion may be biased towards the aligned position.

In accordance with another aspect of the disclosure, a cleaning device for use with an endoscope includes a sleeve and a frame. The sleeve defines a lumen dimensioned to receive a distal end portion of an endoscope and an opening in registration with a lens of the endoscope. The frame includes a supporting portion, an engaging portion pivotably coupled to the supporting portion, and a wiper. The supporting portion is coupled to the sleeve. The wiper is slidable across the lens of the endoscope to remove debris from the lens. The engaging portion is transitionable between an aligned position, in which, the wiper of the frame is placed in a first position on the lens, and an offset position, in which, the engaging portion is pivoted relative to the supporting portion, whereby the wiper is displaced across the lens.

In an aspect, the engaging portion may be distal of the supporting portion.

In another aspect, the supporting portion and the engaging portion may be integrally formed as a single construct.

In yet another aspect, the first and second positions may diametrically oppose each other.

In still yet another aspect, the sleeve may be formed of a flexible or a resilient material to frictionally secure the cleaning device to the endoscope.

In still yet another aspect, the supporting portion may define a cavity. At least a portion of the wiper may extend into the cavity.

In an aspect, the supporting portion may have a contour conforming to a contour of the sleeve.

In another aspect, the wiper may be formed of silicone or rubber.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Figure 1:
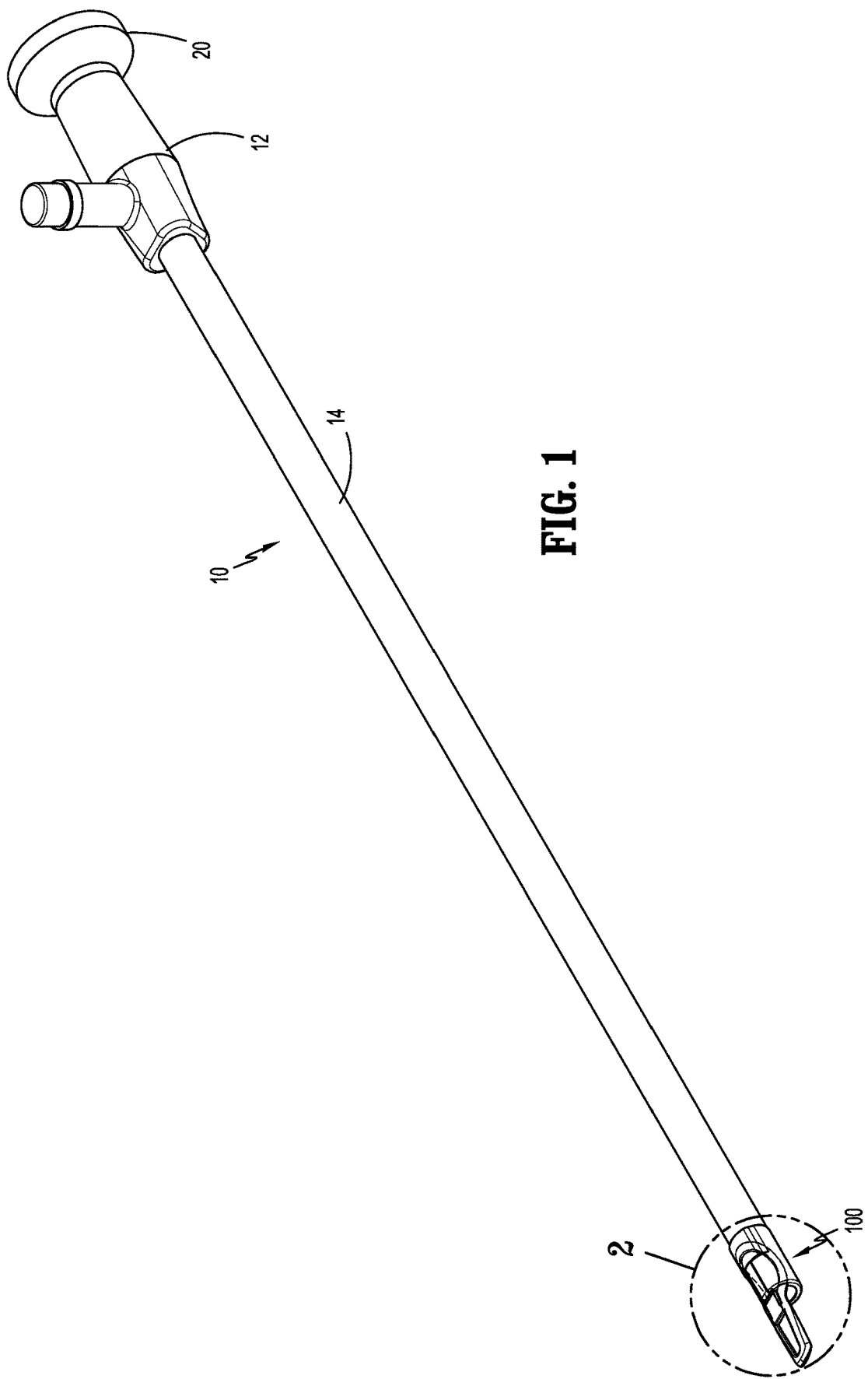
FIG. 1 is a perspective view of a cleaning device in accordance with the disclosure, illustrating the cleaning device mounted on an endoscope.

The endoscope cleaning device disclosed herein is described in detail with reference to the drawings, in which like reference numerals designate identical or corresponding elements in each of the several views.

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 2:
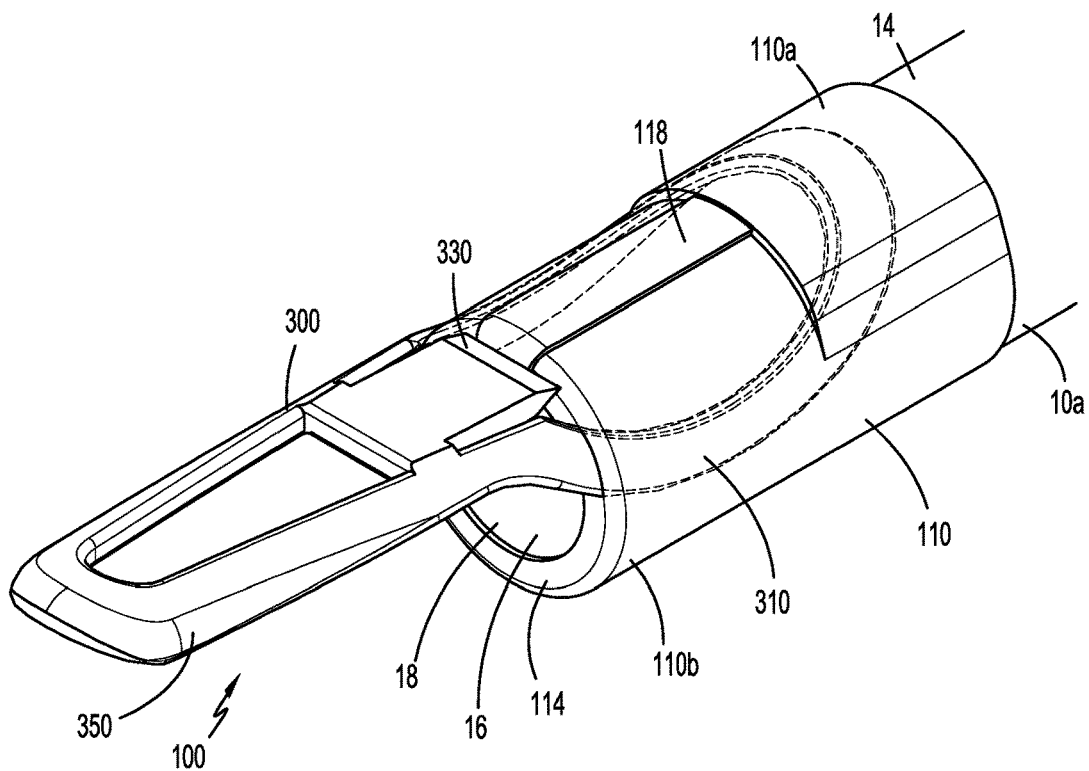
FIG. 2 is an enlarged view of the indicated area of detail of FIG. 1.

In FIGS. 1 and 2, an exemplary in situ lens cleaning device in accordance with the disclosure is shown generally as a cleaning device 100. The cleaning device 100 enables cleaning of a lens 18 of an endoscope 10 during a surgical procedure to maintain a clear image without having to remove the endoscope 10 from the patient's body. In particular, the endoscope 10 includes a housing 12 and an elongated tubular shaft 14 extending distally from the housing 12 and terminating in the lens 18. A distal tip portion 16 of the endoscope 10 includes a number of optical components that produce images of the patient's tissues as known by one skilled in the art. The optical components generally include a window or front element of a lens assembly that is positioned in front of an image sensor or in front of a fiber optic imaging guide that transfers an image to the proximal end of the endoscope 10. Illumination sources such as, e.g., light-emitting diodes, fiber optic or illumination guides, may also be provided. The elongate tubular shaft 14 may be rigid, semi-rigid, or flexible. The housing 12 may include a viewfinder 20 adapted to sight images of a surgical field in the patient, e.g. an abdominal cavity, thoracic cavity, etc., as the position of the endoscope 10 is adjusted to view a particular anatomical structure in the surgical field. A camera is adapted to receive images of the surgical field sighted through the lens 18 and transmit the images to, e.g., an external monitor, on which the images of the surgical field are displayed. That is, a visual display device converts the optical signal into a video signal to produce a video image on the monitor (or for storage on select media). Accordingly, the monitor enables a clinician to view the anatomical structure in the surgical field inside the patient as the surgical procedure is carried out using minimally invasive or endoscopic surgical instruments. Throughout the surgical procedure, condensation, smoke particles, and biological tissue or matter tend to contact and build up on the lens 18 of the endoscope 10. This tends to obscure the images of the surgical field as they are displayed on the monitor. To this end, the cleaning device 100 may be utilized during the surgical procedure to maintain a clear image without having to remove the endoscope 10 from the patient's body, as will be discussed hereinbelow. In particular, the cleaning device 100 may be utilized to remove debris such as, e.g., organic matter and/or moisture, from the lens 18 of the endoscope 10. Further the cleaning device 100 does not requires additional modification to the endoscope 10 for use therewith, as will be discussed below.

FIG. 2 illustrates the cleaning device 100 that is detachably mounted to a distal end portion 10a of the endoscope 10. The cleaning device 100 includes a sleeve or a body 110 having a tubular configuration. The sleeve 110 defines a lumen 112 dimensioned to receive the distal end portion 10a of the endoscope 10. Under such a configuration, the sleeve 110 may be frictionally mounted on various endoscopes having different dimensions. The cleaning device 100 may be made available in different diameters allowing it to be retrofitted to a variety of endoscopes and laparoscopes. It is contemplated that the sleeve 110 may be fixedly secured to the distal end portion 10a of the endoscope 10 through, e.g., ultrasonic welding, adhesive, etc. The sleeve 110 includes proximal and distal end portions 110a, 110b. The proximal end portion 110a defines an aperture 116 receiving the distal-end portion 10a of the endoscope 10. The cleaning device 100 further includes a lip 114 extending radially inwards from the distal end portion 110b of the sleeve 110. The lip 114 defines an opening in registration with the lens 18 of the endoscope 10. The sleeve 110 and the lip 114 may be formed of a flexible or a resilient material such as, e.g., an elastomer. In particular, the sleeve 110 and the lip 114 may be integrally formed as a single construct. In an aspect, the sleeve 110 and the lip 114 may be monolithically formed. The sleeve 110 may be frictionally mounted on the endoscope 10. Under such a configuration, the sleeve 110 may accommodate various sizes or diameters of endoscopes. While the cleaning device 100 is shown as a detachable component separate from the endoscope 10, it is contemplated that the cleaning device 100 may be integrally formed with the endoscope 10 as a single construct. For example, the cleaning device 100 may be over-molded on the elongate tubular shaft 14 of the endoscope 10. When the cleaning device 100 is mounted on the distal end portion 10a of the endoscope 10, the lip 114 is disposed about the lens 18 of the endoscope 10. The lip 114 defines an opening such that the lip 114 engages the distal-most portion of the endoscope 10 without obstructing the lens 18 of the endoscope 10.

Figure 3:
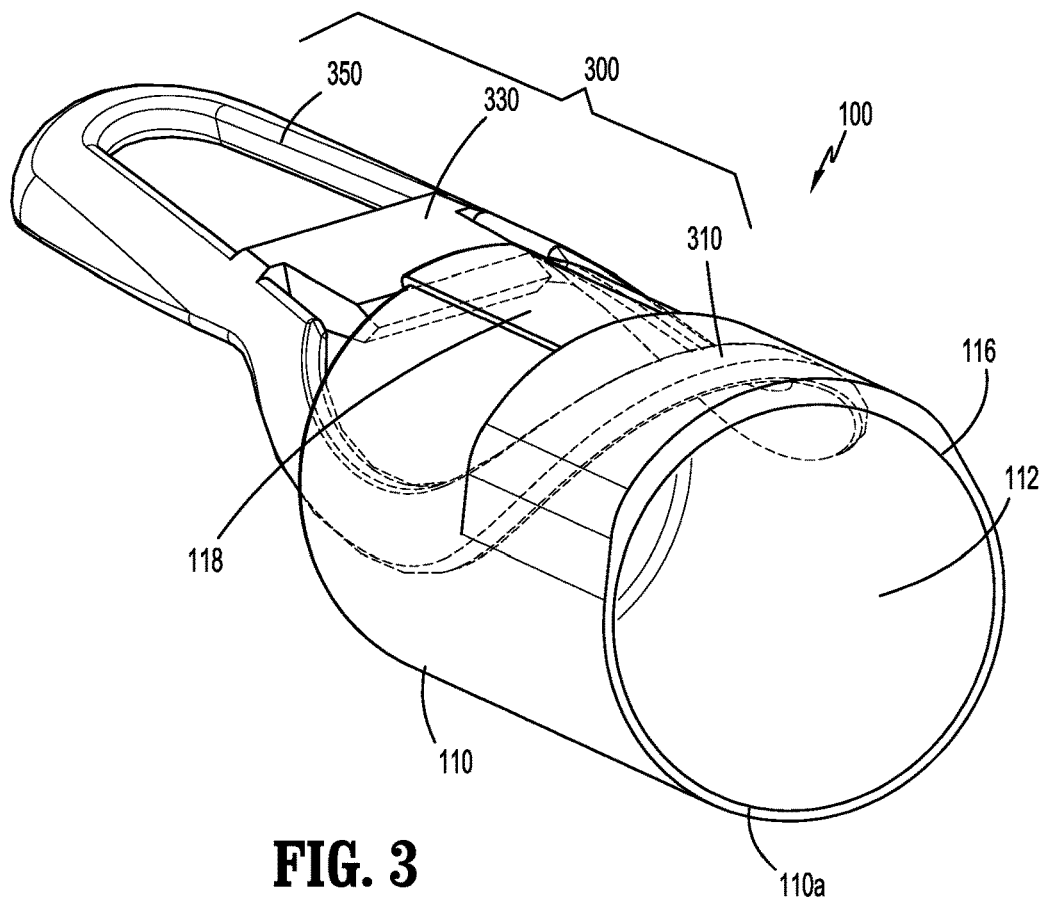
FIG. 3 is a rear perspective view of the cleaning device of FIG. 2.

In order to enhance securement of the sleeve 110 with the endoscope 10, the sleeve 110 may further include a rib 118 (FIGS. 2 and 3). The rib 118 may be more rigid than the sleeve 110 formed of flexible or resilient material. In particular, the rib 118 extends along a length of the sleeve 110 and at least partially extends over the lip 114. Under such a configuration, the rib 118 limits proximal displacement of the sleeve 110 when securing the sleeve 110 on the endoscope 10, which, in turn, ensures proper placement of the lip 114 with the endoscope 10.

The cleaning device 100 further includes a frame 300. FIGS. 2 and 3 illustrate the frame 300 pivotably coupled to the sleeve 110. The frame 300 includes a supporting portion 310 (shown in phantom), a wiper 330, and an engaging portion 350. The supporting portion 310 is secured to the sleeve 110. For example, the supporting portion 310 may be over-molded on the sleeve 110 as a single construct. The supporting portion 310 and the engaging portion 350 may be formed of a flexible or resilient material. In particular, the supporting portion 310 and the engaging portion 350 may be formed as a single construct. In an aspect, the supporting portion 310 and the engaging portion 350 may be monolithically formed. The engaging portion 350 is pivotable relative to the supporting portion 310. In particular, the engaging portion 350 extends distally from the supporting portion 310. The wiper 330 is supported on the engaging portion 350 such that the wiper 330 slides across the lens 18 of the endoscope 10 to remove debris, e.g., organic matter and/or moisture, from the lens 18, when the engaging portion 350 is pivoted, as will be described hereinbelow.

Figure 4:
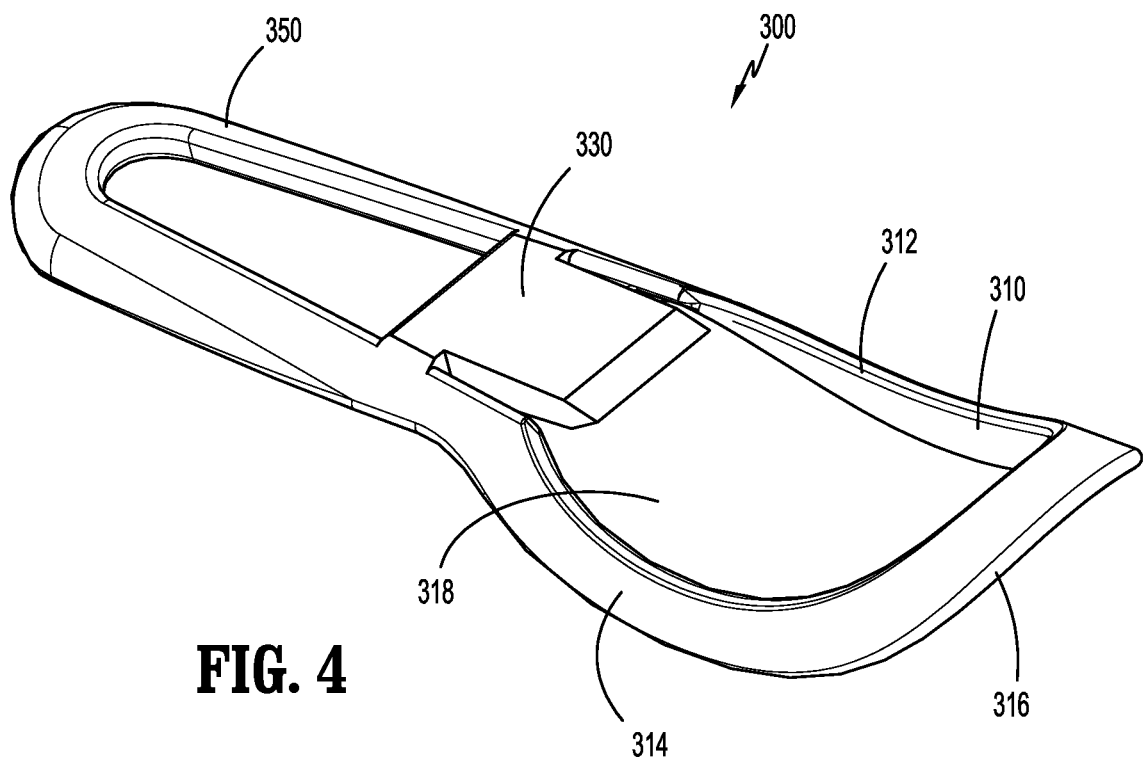
FIG. 4 is a top perspective view of a frame of the cleaning device of FIG. 3.
Figure 5:
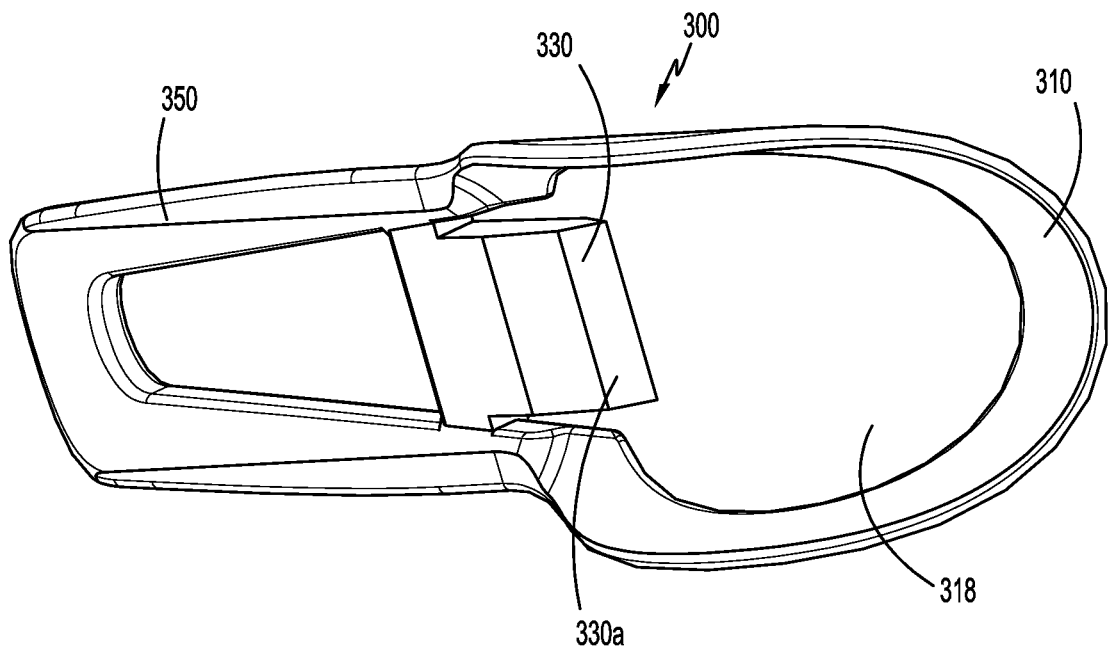
FIG. 5 is a bottom perspective view of the frame of FIG. 4.
Figure 6:
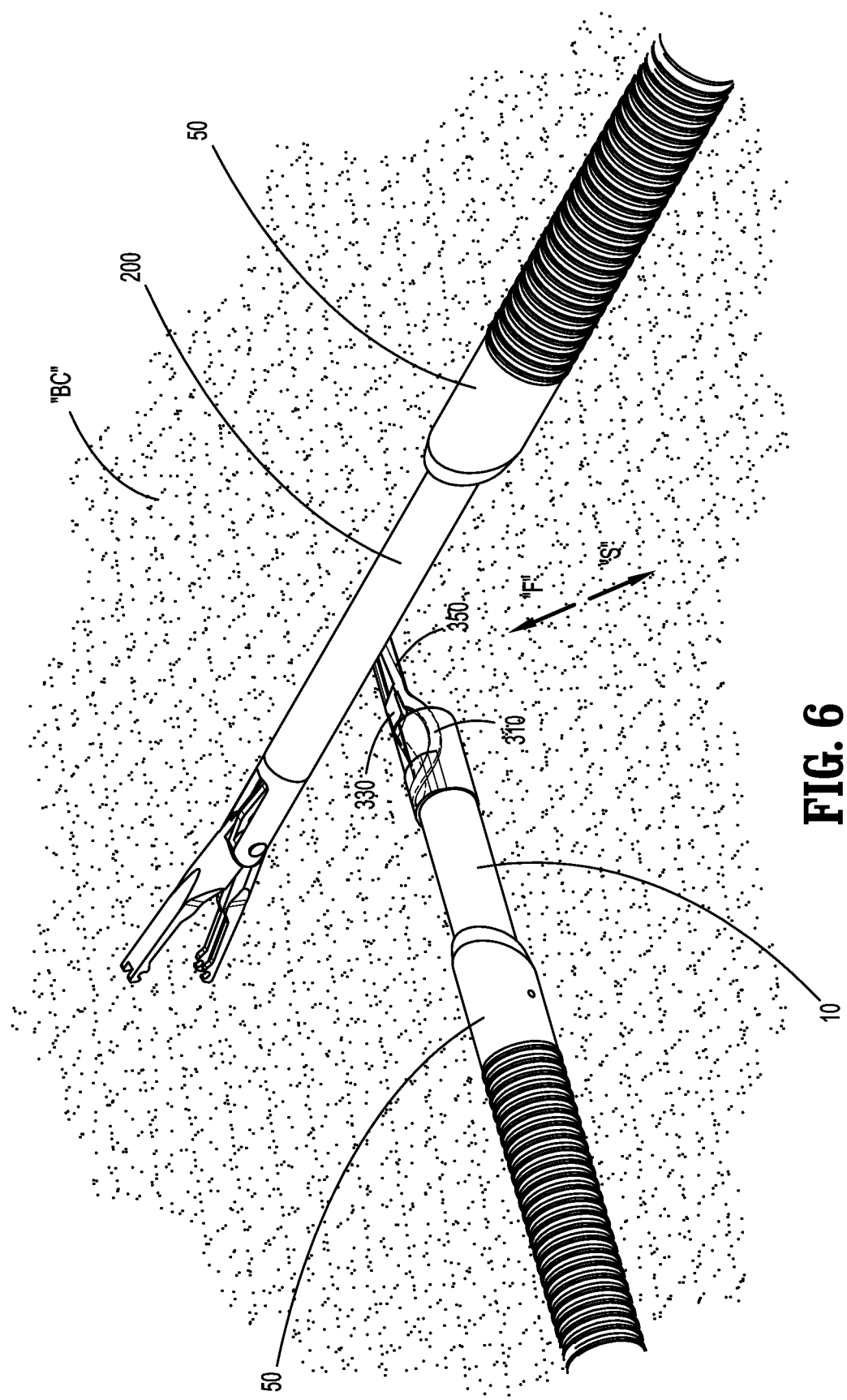
FIGS. 6 and 7 are perspective views of the cleaning device of FIG. 1 mounted on the endoscope, illustrating use of the cleaning device.

FIGS. 4 and 5 illustrate the frame 300 of the cleaning device 100 removed from the sleeve 110. The supporting portion 310 includes opposing lateral portions 312, 314 connected by a connecting portion 316. The opposing lateral portions 312, 314 and the connecting portion 316 define a cavity 318. The supporting portion 310 may be arcuate corresponding to a circular cross-section or contour of the sleeve 110 or the endoscope 10. The engaging portion 350 extends distally from the supporting portion 310 and supports the wiper 330 such that the wiper 330 engages the lens 18 of the endoscope 10. In particular, the wiper 330 may include a tapered edge 330a configured to enhance removal of the debris from the lens 18. The engaging portion 350 is pivotable relative to the supporting portion 310. Under such a configuration, when the engaging portion 350 pivots relative to the supporting portion 310, the wiper 330 slides across the lens 18 to remove debris therefrom. In this manner, the wiper 330 is transitionable from an initial position in which, the wiper 330 and the engaging portion 350 are in registration with the rib 118, and an offset position, in which, the wiper 330 and the engaging portion 350 are offset from the rib 118. In this manner, the wiper 330 is movable between two diametrically opposing positions on the lens 18. Further, the frame 300 may be formed of a resilient or flexible material to bias the wiper 330 to the initial position. The engaging portion 350 extends from the supporting portion 310 and may be displaced by another surgical instrument such as, e.g., the surgical clip applier 200 (FIG. 6). The engaging portion 350 may be pushed against another surgical instrument or against tissue to transition the wiper 330 from the initial position to the offset position.

Figure 7:
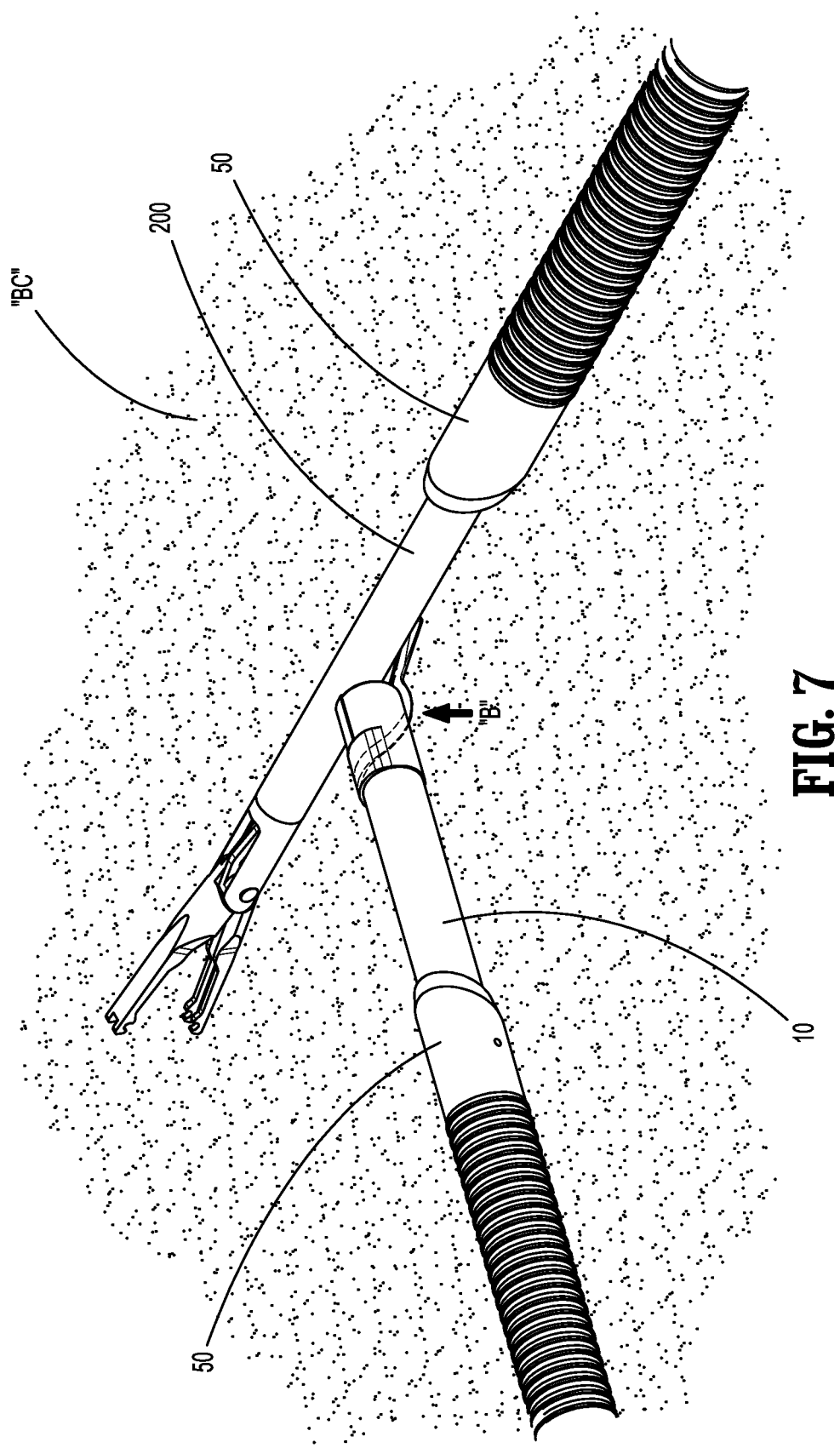

FIGS. 6 and 7 illustrate the use of the cleaning device 100 with the endoscope 10. Prior to use, the cleaning device 100 may be mounted on the distal end portion 10a of the endoscope 10. The clinician may utilize one or more cannulas 50. The cannulas 50 are configured to permit access to a surgical site such as, e.g., an insufflated abdominal cavity, during a laparoscopic procedure to permit the introduction of a surgical instrument such as, e.g., the endoscope or a surgical clip applier 200, for performing various surgical tasks on internal organs within the cavity.

Initially, the endoscope 10 is inserted into a body cavity "BC" through a cannula 50, and the surgical clip applier 200 is inserted into the body cavity "BC" through a second cannula 50. The surgical clip applier 200 may be utilized as needed by the clinician and the lens 18 of the endoscope 10 may be manipulated as needed to be placed adjacent the surgical site to provide a visual aid to the clinician. When the lens 18 of the endoscope 10 is obscured by debris, e.g., organic matter and/or moisture, the clinician may place the engaging portion 350 of the cleaning device 100 against another surgical instrument such as, e.g., the surgical clip applier 200. At this time, the endoscope 10 may be manipulated to displace supporting portion 310 in the direction of an arrow "F" such that the wiper 330 slides across the lens 18. Alternatively, the endoscope 10 may be kept stationary and the clinician may manipulate the surgical clip applier 200 to displace the engaging portion 350 of the cleaning device 100 in the direction of the arrow "S". Such movements advance the wiper 330 of the cleaning device 100 across the lens 18 of the endoscope 10, thereby removing debris on the lens 18. While FIGS. 6 and 7 are shown to advance the wiper 330 of the cleaning device 100 across the lens 18 of the endoscope 10, the engaging portion 350 may be pushed against, e.g., tissue, to advance the wiper 330 of the cleaning device 100 across the lens 18 of the endoscope 10 without utilizing a separate instrument such as, e.g., the surgical clip applier 200. In this manner, the lens 18 of the endoscope 10 may be cleaned without removing the endoscope 10 from the body cavity "BC." The cleaning of the lens 18 may be repeated as needed during the surgical procedure. It is also envisioned that the cleaning device 100 may be adapted for use with a robotic surgical system.

While specific structures have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A surgical kit comprising:
   an endoscope having a lens at a distal end portion of the endoscope; and
   a cleaning device including:
      a sleeve defining a lumen dimensioned to receive the distal end portion of the endoscope;
      a lip extending radially inwards from the sleeve;
      a rib extending along a length of the sleeve, a distal portion of the rib extending over the lip, the distal portion being configured to inhibit proximal movement of the sleeve relative to the endoscope; and
      a frame including a supporting portion, a wiper, and an engaging portion, the supporting portion secured to the sleeve, the engaging portion pivotably coupled to the supporting portion and extending distally from the supporting portion, the engaging portion supporting the wiper for movement as a single construct,
   wherein the engaging portion and the wiper are transitionable between an aligned position and an offset position, the aligned position defined by the engaging portion and the wiper being substantially parallel to a longitudinal axis of the sleeve and the offset position defined by the engaging portion and the wiper being at an acute angle with respect to the longitudinal axis such that the wiper is displaced across the lens to remove debris from the lens.

2. The surgical kit according to claim 1, wherein the cleaning device is integrally formed as a single construct.

3. The surgical kit according to claim 1, wherein the supporting portion and the engaging portion are monolithically formed.

4. The surgical kit according to claim 1, wherein the sleeve is formed of a flexible or resilient material.

5. The surgical kit according to claim 1, wherein the sleeve is formed of an elastomer to detachably secure the sleeve to the endoscope.

6. The surgical kit according to claim 1, wherein the lip defines an opening in registration with the lens of the endoscope.

7. The surgical kit according to claim 6, wherein the distal portion of the rib extends transversely to the rib thereby limiting proximal displacement of the sleeve when the lip engages the endoscope.

8. The surgical kit according to claim 1, wherein the supporting portion of the frame includes opposing lateral portions interconnected by a connecting portion.

9. The surgical kit according to claim 1, wherein the supporting portion includes an arcuate profile corresponding to contour of the sleeve.

10. The surgical kit according to claim 1, wherein the supporting portion is over-molded to the sleeve.

11. The surgical kit according to claim 1, wherein the wiper includes a tapered edge.

12. The surgical kit according to claim 1, wherein the engaging portion is biased towards the aligned position.

13. A cleaning device for use with an endoscope comprising:
   a sleeve defining a longitudinal axis and a lumen dimensioned to receive a distal end portion of an endoscope and an opening in registration with a lens of the endoscope;
   a rib coupled to the sleeve, a distal portion of the rib extending into the lumen, the distal portion being configured to inhibit proximal movement of the sleeve relative to an endoscope disposed in the sleeve; and
   a frame including a supporting portion, an engaging portion pivotably coupled to the supporting portion, and a wiper, the supporting portion coupled to the sleeve, the wiper slidable across the lens of the endoscope to remove debris from the lens,
   wherein the engaging portion and the wiper are transitionable between an aligned position and an offset position, the aligned position defined by the engaging portion and the wiper being substantially parallel to the longitudinal axis and the offset position defined by the engaging portion and the wiper being at an acute angle with respect to the longitudinal axis such that the wiper is pivoted relative to the supporting portion, whereby the wiper is displaced across the lens.

14. The cleaning device according to claim 13, wherein the engaging portion is distal of the supporting portion.

15. The cleaning device according to claim 13, wherein the supporting portion and the engaging portion are integrally formed as a single construct.

16. The cleaning device according to claim 13, wherein the first and second positions diametrically oppose each other.

17. The cleaning device according to claim 13, wherein the sleeve is formed of a flexible or a resilient material to frictionally secure the cleaning device to the endoscope.

18. The cleaning device according to claim 13, wherein the supporting portion defines a cavity, at least a portion of the wiper extending into the cavity.

19. The cleaning device according to claim 13, wherein the supporting portion has a contour conforming to a contour of the sleeve.

20. The cleaning device according to claim 13, wherein the wiper is formed of silicone or rubber.

* * * * *